US010722720B2

(12) United States Patent
Stahmann et al.

(10) Patent No.: US 10,722,720 B2
(45) Date of Patent: Jul. 28, 2020

(54) METHODS AND SYSTEMS FOR IMPROVED COMMUNICATION BETWEEN MEDICAL DEVICES

(71) Applicant: Cardiac Pacemakers, Inc., St. Paul, MN (US)

(72) Inventors: Jeffrey E. Stahmann, Ramsey, MN (US); William J. Linder, Golden Valley, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 16/014,760

(22) Filed: Jun. 21, 2018

(65) Prior Publication Data

US 2018/0304085 A1    Oct. 25, 2018

Related U.S. Application Data

(63) Continuation of application No. 14/592,595, filed on Jan. 8, 2015, now abandoned.
(Continued)

(51) Int. Cl.
*A61N 1/372* (2006.01)
*A61B 5/00* (2006.01)
(Continued)

(52) U.S. Cl.
CPC ........ *A61N 1/37217* (2013.01); *A61B 5/0028* (2013.01); *A61N 1/37288* (2013.01);
(Continued)

(58) Field of Classification Search
CPC .................................................. A61N 1/37217
See application file for complete search history.

(56) References Cited

U.S. PATENT DOCUMENTS

| 3,835,864 A | 9/1974 | Rasor et al. |
| 3,943,936 A | 3/1976 | Rasor et al. |

(Continued)

FOREIGN PATENT DOCUMENTS

| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)
(Continued)

*Primary Examiner* — William J Levicky
(74) *Attorney, Agent, or Firm* — Seager, Tufte & Wickhem LLP

(57) ABSTRACT

At least one of a first medical device and a second medical device may be implanted within a patient while the second medical device may optionally be proximate but external to the patient. At least one of the medical devices has an antenna having at least two electrodes and at least one of the medical devices has an antenna having at least three electrodes. The medical devices can communicate via conducted communication through the patient's tissue between a first pair of electrodes and a second pair of electrodes. At least one of the pairs of electrodes can be selected in accordance with the signal strength of the communication vector between the first and second pairs of electrodes.

16 Claims, 13 Drawing Sheets

Related U.S. Application Data

(60) Provisional application No. 61/926,101, filed on Jan. 10, 2014.

(51) Int. Cl.
*H04B 13/00* (2006.01)
*A61N 1/36* (2006.01)
*A61B 5/0464* (2006.01)
*A61N 1/362* (2006.01)
*A61N 1/375* (2006.01)

(52) U.S. Cl.
CPC .......... *H04B 13/005* (2013.01); *A61B 5/0464* (2013.01); *A61B 5/4836* (2013.01); *A61N 1/362* (2013.01); *A61N 1/3605* (2013.01); *A61N 1/3756* (2013.01); *A61N 1/37223* (2013.01); *A61N 1/37252* (2013.01)

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | Decoriolis et al. |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,466,246 A | 11/1995 | Silvian |
| 5,468,254 A | 11/1995 | Hahn et al. |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,591,214 A | 1/1997 | Lu |
| 5,620,466 A | 4/1997 | Haefner et al. |
| 5,634,938 A | 6/1997 | Swanson et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras et al. |
| 5,954,757 A | 9/1999 | Gray |
| 5,978,713 A | 11/1999 | Prutchi et al. |
| 5,991,660 A | 11/1999 | Goyal |
| 5,999,848 A | 12/1999 | Gord et al. |
| 5,999,857 A | 12/1999 | Weijand et al. |
| 6,026,320 A | 2/2000 | Carlson et al. |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |

(56) References Cited

U.S. PATENT DOCUMENTS

| | | |
|---|---|---|
| 6,164,284 A | 12/2000 | Schulman et al. |
| 6,167,310 A | 12/2000 | Grevious |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,298,271 B1 | 10/2001 | Weijand |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,445,955 B1* | 9/2002 | Michelson ......... A61N 1/37211 607/59 |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,110,824 B2 | 9/2006 | Amundson et al. |
| 7,120,504 B2 | 10/2006 | Osypka |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,790 B2 | 4/2007 | Thompson et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |

(56) References Cited

U.S. PATENT DOCUMENTS

| | | |
|---|---|---|
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,175 B2 | 11/2011 | Rowlandson |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |

(56) References Cited

U.S. PATENT DOCUMENTS

| | | |
|---|---|---|
| 8,233,985 B2 | 7/2012 | Bulkes et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,527,068 B2 | 9/2013 | Ostroff |
| 8,532,790 B2 | 9/2013 | Griswold |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,773 B2 | 5/2014 | Willis et al. |
| 8,738,147 B2 | 5/2014 | Hastings et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,500 B2 | 12/2014 | Smith et al. |
| 8,903,513 B2 | 12/2014 | Ollivier |
| 8,914,131 B2 | 12/2014 | Bomzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,795 B1 | 4/2015 | Yang |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |

(56) References Cited

U.S. PATENT DOCUMENTS

| | | |
|---|---|---|
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bomzin et al. |
| 9,433,368 B2 | 9/2016 | Stahmann et al. |
| 9,433,780 B2 | 9/2016 | Régnier et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0041866 A1 | 3/2003 | Linberg et al. |
| 2003/0088278 A1 | 5/2003 | Bardy et al. |
| 2003/0097153 A1 | 5/2003 | Bardy et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0027508 A1 | 2/2007 | Cowan |
| 2007/0043393 A1* | 2/2007 | Brockway ............ A61N 1/056 607/4 |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0275521 A1* | 11/2008 | Warren ............... A61N 1/3622 607/17 |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |

(56) References Cited

U.S. PATENT DOCUMENTS

| | | |
|---|---|---|
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204170 A1 | 8/2009 | Hastings et al. |
| 2009/0210024 A1 | 8/2009 | M |
| 2009/0216292 A1 | 8/2009 | Pless et al. |
| 2009/0228073 A1 | 9/2009 | Scholten |
| 2009/0234407 A1 | 9/2009 | Hastings et al. |
| 2009/0234411 A1 | 9/2009 | Sambelashvili et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0312309 A1 | 12/2010 | Harding |
| 2011/0004088 A1 | 1/2011 | Grossman |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160557 A1* | 6/2011 | Cinbis ............... A61N 1/37217 600/374 |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109258 A1 | 5/2012 | Cinbis |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0170471 A1 | 7/2012 | Brown |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0281814 A1 | 10/2013 | Tilt |
| 2013/0282070 A1 | 10/2013 | Cowan et al. |

(56) References Cited

U.S. PATENT DOCUMENTS

| | | |
|---|---|---|
| 2013/0282073 A1 | 10/2013 | Cowan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0257324 A1 | 9/2014 | Fain |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishier et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006086435 A3 | 8/2006 |
| WO | 2006113659 A1 | 10/2006 |
| WO | 2006124833 A3 | 5/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |

OTHER PUBLICATIONS

Hachisuka et al., "Development and Performance Analysis of an Intra-Body Communication Device," The 12th International Conference on Solid State Sensors, Actuators and Microsystems, vol. 4A1.3, pp. 1722-1725, 2003.
Seyedi et al., "A Survey on Intrabody Communications for Body Area Network Application," IEEE Transactions on Biomedical Engineering, vol. 60(8): 2067-2079, 2013.

(56) References Cited

OTHER PUBLICATIONS

Wegmüller, "Intra-Body Communication for Biomedical Sensor Networks," Diss. ETH, No. 17323, 1-173, 2007.
Notification of Transmittal of the International Search Report and the Written Opinion of the International Searching Authority, or the Declaration, Jan. 29, 2016, 15 pages.
Spickler et al., "Totally Self-Contained Intracardiac Pacemaker," Journal of Electrocardiology, vol. 3(3&4): 324-331, 1970.
"Instructions for Use System 1, Leadless Cardiac Pacemaker (LCP) and Delivery Catheter," Nanostim Leadless Pacemakers, pp. 1-28, 2013.

\* cited by examiner

METHODS AND SYSTEMS FOR IMPROVED COMMUNICATION BETWEEN MEDICAL DEVICES

RELATED APPLICATIONS

This application is a continuation of U.S. application Ser. No. 14/592,595, filed on Jan. 8, 2015, which claims priority to U.S. Provisional Application No. 61/926,101 filed on Jan. 10, 2014, the disclosures of each incorporated herein by reference.

TECHNICAL FIELD

The present disclosure generally relates to communication between medical devices, and more particularly, to methods and systems for improved communication between medical devices.

BACKGROUND

Pacing instruments can be used to treat patients suffering from various heart conditions that may result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) can be implanted in a patient's body. Such devices may monitor and provide electrical stimulation to the heart to help the heart operate in a more normal, efficient and/or safe manner. In some cases, a patient may have multiple devices that operate together to detect and/or treat various conditions.

SUMMARY

The present disclosure generally relates to communication between medical devices, and more particularly, to methods and systems for improved communication between medical devices. For example, a first medical device and a second medical device may be implanted within a patient, or the first medical device may be implanted within the patient and the second medical device may be proximate but external to the patient. At least one of the medical devices may have an antenna with at least two electrodes, and at least one of the medical devices may have an antenna with at least three electrodes. The medical devices may communicate by transmitting signals from two of the electrodes of the transmitting medical device to at least two electrodes of the receiving medical device. It is contemplated that the medical devices may communicate via radiofrequency (RF) communication, inductive coupling, conducted communication, or any other suitable communication technique.

It will be appreciated that the relative signal strength between any two pairs of electrodes, such as a first pair of electrodes belonging to the transmitting medical device and a second pair of electrodes belonging to the receiving medical device, may depend in part on the orientation of the receiving electrodes relative to the electromagnetic field produced by the transmitting electrodes. The system may be configured to select a particular pair of electrodes for the transmitting medical device and/or the receiving medical device in order help improve the signal strength of communication between the devices. The different combination of electrodes that may be used for communication between medical devices can each be referred to a "communication vector". In some instances, various communication vectors may be tested, and the communication vector that produces the highest relative signal strength and/or signal-to-noise ratio may be selected for subsequent communication. Various communication vectors may be re-tested periodically, upon command, when the relative signal strength and/or signal-to-noise ratio falls below a threshold, when the relative signal strength and/or signal-to-noise ratio changes by a threshold, and/or at any other suitable time as desired.

An example method of communicating between a first medical device having a first antenna and a second medical device having a second antenna is disclosed. The first medical device is implanted within a patient and the second medical device is proximate to the patient, and the first antenna and/or the second antenna has at least three electrodes and the other antenna has at least two electrodes. The example method comprises:

selecting a first electrode pair of the antenna that has at least three electrodes;

at least one of sending and receiving a conducted communication signal through tissue of the patient between the first electrode pair of the antenna that has at least three electrodes and two of the electrodes of the other antenna;

selecting a second electrode pair of the antenna that has at least three electrodes, wherein the second electrode pair is different from the first electrode pair; and sending a conducted communication signal through tissue of the patient between the second electrode pair of the antenna that has at least three electrodes and two electrodes of the other antenna.

Alternatively or additionally to any of the embodiments above, the method may further include:

monitoring a measure related to a signal to noise ratio of the conducted communication signal using the first electrode pair;

if the measure related to a signal to noise ratio of the conducted communication signal using the first electrode pair falls below a threshold, then:
  selecting the second electrode pair of the antenna that has at least three electrodes; and
  sending the conducted communication signal through tissue of the patient between the second electrode pair of the antenna that has at least three electrodes and the two electrodes of the other antenna.

Alternatively or additionally to any of the embodiments above, the method may further include:

determining a first measure related to a signal to noise ratio of the conducted communication signal using the first electrode pair;

determining a second measure related to a signal to noise ratio of the conducted communication signal using the second electrode pair; and selecting the first electrode pair or the second electrode pair for subsequent communication based on the first measure and the second measure.

Alternatively or additionally to any of the embodiments above, the second medical device may be implanted within the patient but spaced from the first medical device.

Alternatively or additionally to any of the embodiments above, the second medical device may be disposed outside of the patient and the second antenna is positioned on a skin surface of the patient.

Alternatively or additionally to any of the embodiments above, the antenna that has at least three electrodes may comprise three electrodes that are arranged in a triangular configuration.

Alternatively or additionally to any of the embodiments above, the antenna that has at least three electrodes may comprise four electrodes that are arranged in a rectangular configuration.

Alternatively or additionally to any of the embodiments above, the antenna that has at least three electrodes may comprise four electrodes that are arranged in a kite configuration.

Another example method of communicating between a first medical device having a first antenna with at least two electrodes and a second medical device having a second antenna with at least three electrodes comprises:

testing communication vectors between the at least two electrodes of the first antenna and each of a plurality of pairs of electrodes of the at least three electrodes of the second antenna;

selecting a communication vector based on signal strengths of each of the communication vectors; and at least one of sending and receiving a conducted communication between the first medical device and the second medical device using the selected communication vector.

Alternatively or additionally to any of the embodiments above, the first medical device may comprise an implanted medical device and the second medical device may comprise an external device.

Alternatively or additionally to any of the embodiments above, the first medical device may comprise an external device and the second medical device may comprise an implanted medical device.

Alternatively or additionally to any of the embodiments above, the first medical device may comprise a first implanted medical device and the second medical device may comprise a second implanted medical device.

Alternatively or additionally to any of the embodiments above, selecting a communication vector may comprise selecting the communication vector with the strongest signal strength.

Alternatively or additionally to any of the embodiments above, selecting a communication vector may comprise not selecting the communication vector with the weakest signal strength.

An example communications system is also disclosed. The example communications system comprises:

a first medical device in communication with a first antenna having at least two electrodes; and a second medical device in communication with a second antenna having at least three electrodes;

wherein at least one of the first medical device and the second medical device is configured to:

test communication vectors between the at least two electrodes of the first antenna and at least two pairs of the at least three electrodes of the second antenna;

select a communication vector from the tested communication vectors; and at least one of send and receive a conducted communication along the selected communication vector.

Alternatively or additionally to any of the embodiments above, the at least three electrodes may comprise three electrodes that are arranged in a triangular configuration.

Alternatively or additionally to any of the embodiments above, the at least three electrodes may comprise four electrodes that are arranged in a rectangular configuration.

Alternatively or additionally to any of the embodiments above, the at least three electrodes may comprise four electrodes that are arranged in a kite configuration.

Alternatively or additionally to any of the embodiments above, at least one of the first medical device and the second medical device may be implanted within a patient.

Alternatively or additionally to any of the embodiments above, the first medical device is a leadless cardiac pacemaker (LCP).

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE FIGURES

The disclosure may be more completely understood in consideration of the following description of various illustrative embodiments in connection with the accompanying drawings, in which.

Figure 1:
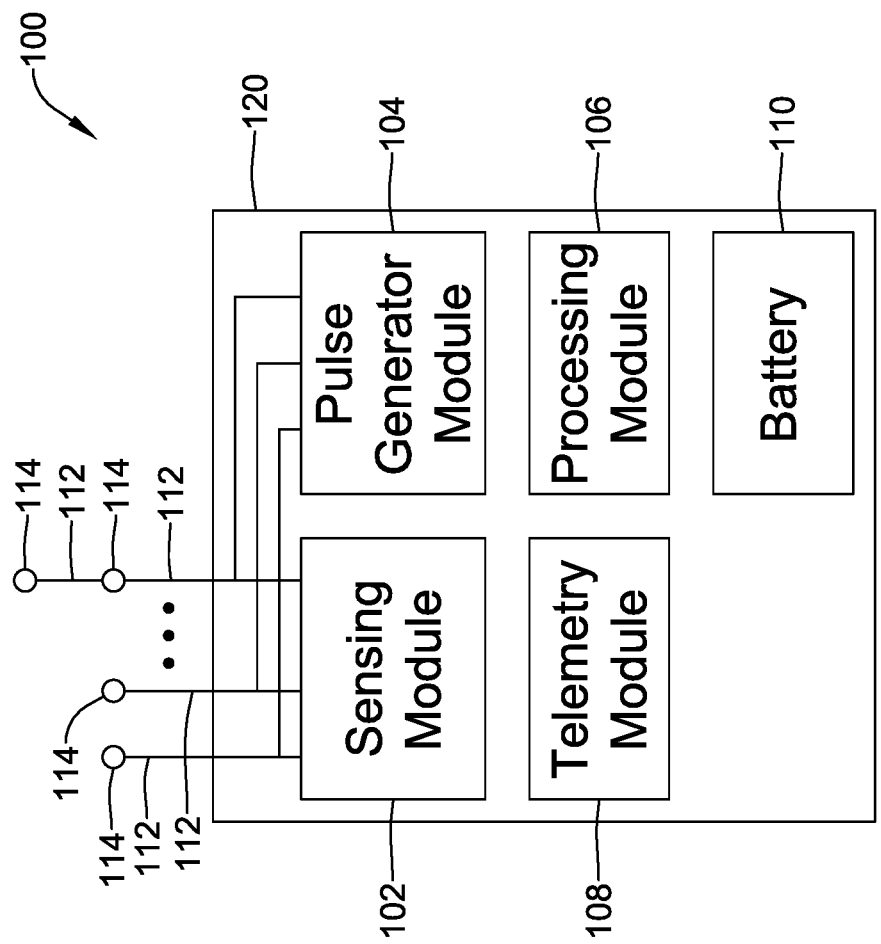
FIG. 1 illustrates a block diagram of an exemplary medical device that may be used in accordance with various examples of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DETAILED DESCRIPTION

The following description should be read with reference to the drawings in which similar elements in different drawings are numbered the same. The description and the drawings, which are not necessarily to scale, depict illustrative embodiments and are not intended to limit the scope of the disclosure.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect the contractility of their hearts. For example, some hearts may develop diseased tissues that no longer generate or conduct intrinsic electrical signals. In some examples, diseased cardiac tissues conduct electrical signals at differing rates, thereby causing an unsynchronized and inefficient contraction of the heart. In other examples, a heart may generate intrinsic signals at such a low rate that the heart rate becomes dangerously low. In still other examples, a heart may generate electrical signals at an unusually high rate. In some cases such an abnormality can develop into a fibrillation state, where the contraction of the patient's heart is almost completely desynchronized and the heart pumps very little to no blood.

Many medical device systems have been developed to assist patients who experience such abnormities. For example, systems have been developed to sense intrinsic cardiac electrical signals and, based on the sensed electrical signals, determine whether the patient is suffering from one or more arrhythmias. Such systems may also include the ability to deliver electrical stimulation to the heart of the patient in order to treat the detected arrhythmias. In one example, some medical device systems include the ability to identify when the heart is beating at too low of a rate, termed bradycardia. Such systems may deliver electrical stimulation therapy, or "pacing" pulses, that cause the heart to contract at a higher, safer rate. Some medical device systems are able to determine when a heart is beating at too fast of a rate, termed tachycardia. Such systems may further include one or more anti-tachycardia pacing (ATP) therapies. One such ATP therapy includes delivering electrical stimulation pulses to the heart at a rate faster than the intrinsically generated signals. Although this may temporarily cause the heart to beat faster, such a stimulation protocol may cause the heart to contract in response to the delivered pacing pulses as opposed to the intrinsically generated signals. The ATP therapy may then slow down the rate of the delivered pacing pulses, thereby reducing the heart rate to a lower, safer level.

Other medical device systems may be able to detect fibrillation states and asynchronous contractions. For example, based on the sensed signals, some systems may be able to determine when the heart is in a fibrillation state. Such systems may further be configured to treat such fibrillation states with electrical stimulation therapy. One such therapy includes deliver of a relatively large amount of electrical energy to the heart (a "defibrillation pulse") with the goal of overpowering any intrinsically generated signals. Such a therapy may "reset" the heart, from an electrical standpoint, which may allow for normal electrical processes to take over. Other medical systems may be able to sense that intrinsically generated signals are generated at differing times or that the heart conducts such signals at differing rates. These abnormalities may result in an unsynchronized, inefficient cardiac contraction. The system may further include the ability to administer one or more cardiac resynchronization therapies (CRTs). One such CRT may include delivering electrical stimulation to the heart at differing locations on and/or within the heart. Such methods may help the disparate parts of the heart to contract near simultaneously, or in a synchronized manner if the system delivers the electrical stimulation to the disparate locations at differing times.

The present disclosure relates generally to systems and methods for coordinating detection and/or treatment of abnormal heart activity using multiple implanted devices within a patient. In some instances, a medical device system may include a plurality of devices for detecting cardiac arrhythmias and delivering electrical stimulation therapy. For example, illustrative systems may include devices such as subcutaneous cardioverter-defibrillators (S-ICD), external cardioverter-defibrillators, implantable cardiac pacemakers (ICP), leadless cardiac pacemakers (LCPs), and/or diagnostic only devices (devices that may sense cardiac electrical signals and/or determine arrhythmias but do not deliver electrical stimulation therapies).

FIG. 1 illustrates a block diagram of an exemplary medical device 100 (referred to hereinafter as, MD 100) that may be used in accordance with various examples of the present disclosure. In some cases, the MD 100 may be used for sensing intrinsic cardiac activity, determining occurrences of arrhythmias, and delivering electrical stimulation in response to determining an occurrence of an arrhythmia. In some instances, MD 100 can be implanted within a patient's body, at a particular location (e.g., in close proximity to the patient's heart), to sense and/or regulate the cardiac activity of the heart. In other examples, MD 100 may be located externally to a patient to sense and/or regulate the cardiac activity of the heart. In one example, cardiac contractions generally result from electrical signals that are intrinsically generated by a heart. These electrical signals conduct through the heart tissue, causing the muscle cells of the heart to contract. MD 100 may include features that allow MD 100 to sense such electrical signals and/or other physical parameters (e.g. mechanical contraction, heart sounds, blood pressure, blood-oxygen levels, etc.) of the heart. Such electrical signals and/or physical properties may be considered "cardiac activity." MD 100 may include the ability to determine occurrences of arrhythmias based on the sensed cardiac activity. In some examples, MD 100 may be able to deliver electrical stimulation to the heart in order to treat any detected arrhythmias. For example, MD 100 may be configured to deliver electrical stimulation, pacing pulses, defibrillation pulses, and/or the like in order to implement one or more therapies, such as bradycardia therapy, ATP therapy, CRT, defibrillation, or other electrical stimulation therapies.

FIG. 1 is an illustration of an example medical device 100. The illustrative MD 100 may include a sensing module 102, a pulse generator module 104, a processing module 106, a telemetry module 108, and a battery 110, all housed within a housing 120. MD 100 may further include leads 112, and electrodes 114 attached to housing 120 and in electrical communication with one or more of the modules 102, 104, 106, and 108 housed within housing 120.

Leads 112 may be connected to and extend away from housing 120 of MD 100. In some examples, leads 112 are implanted on or within the heart of the patient. Leads 112 may contain one or more electrodes 114 positioned at various locations on leads 112 and distances from housing 120. Some leads 112 may only include a single electrode 114 while other leads 112 may include multiple electrodes 114. Generally, electrodes 114 are positioned on leads 112 such that when leads 112 are implanted within the patient, one or more electrodes 114 are in contact with the patient's cardiac tissue. Accordingly, electrodes 114 may conduct intrinsically generated electrical signals to leads 112. Leads 112 may, in turn, conduct the received electrical signals to one or more modules 102, 104, 106, and 108 of MD 100. In a similar manner, MD 100 may generate electrical stimulation, and leads 112 may conduct the generated electrical stimulation to electrodes 114. Electrodes 114 may then conduct the electrical signals to the cardiac tissue of the patient. When discussing sensing intrinsic signals and delivering electrical stimulation, this disclosure may consider such conduction implicit in those processes.

Sensing module 102 may be configured to sense the cardiac electrical activity of the heart. For example, sensing module 102 may be connected to leads 112 and electrodes 114 through leads 112 and sensing module 102 may be configured to receive cardiac electrical signals conducted through electrodes 114 and leads 112. In some examples, leads 112 may include various sensors, such as accelerometers, blood pressure sensors, heart sound sensors, blood-oxygen sensors, and other sensors which measure physiological parameters of the heart and/or patient. In other examples, such sensors may be connected directly to sensing module 102 rather than to leads 112. In any case, sensing module 102 may be configured to receive such signals produced by any sensors connected to sensing module 102, either directly or through leads 112. Sensing modules 102 may additionally be connected to processing module 106 and may be configured to communicate such received signals to processing module 106.

Pulse generator module 104 may be connected to electrodes 114. In some examples, pulse generator module 104 may be configured to generate an electrical stimulation signals to provide electrical stimulation therapy to the heart. For example, pulse generator module 104 may generate such a signal by using energy stored in battery 110 within MD 100. Pulse generator module 104 may be configured to generate electrical stimulation signals in order to provide one or multiple of a number of different therapies. For example, pulse generator module 104 may be configured to generate electrical stimulation signals to provide bradycardia therapy, tachycardia therapy, cardiac resynchronization therapy, and fibrillation therapy. Bradycardia therapy may include generating and delivering pacing pulses at a rate faster than the intrinsically generated electrical signals in order to try to increase the heart rate. Tachycardia therapy may include ATP therapy as described herein. Cardiac resynchronization therapy may include CRT therapy also described herein. Fibrillation therapy may include delivering a fibrillation pulse to try to override the heart and stop the fibrillation state. In other examples, pulse generator 104 may be configured to generate electrical stimulation signals to provide electrical stimulation therapies different than those described herein to treat one or more detected arrhythmias.

Processing module 106 can be configured to control the operation of MD 100. For example, processing module 106 may be configured to receive electrical signals from sensing module 102. Based on the received signals, processing module 106 may be able to determine occurrences of arrhythmias. Based on any determined arrhythmias, processing module 106 may be configured to control pulse generator module 104 to generate electrical stimulation in accordance with one or more therapies to treat the determined one or more arrhythmias. Processing module 106 may further receive information from telemetry module 108. In some examples, processing module 106 may use such received information in determining whether an arrhythmia is occurring or to take particular action in response to the information. Processing module 106 may additionally control telemetry module 108 to send information to other devices.

In some examples, processing module 106 may include a pre-programmed chip, such as a very-large-scale integration (VLSI) chip or an application specific integrated circuit (ASIC). In such embodiments, the chip may be pre-programmed with control logic in order to control the operation of MD 100. By using a pre-programmed chip, processing module 106 may use less power than other programmable circuits while able to maintain basic functionality, thereby increasing the battery life of MD 100. In other examples, processing module 106 may include a programmable microprocessor. Such a programmable microprocessor may allow a user to adjust the control logic of MD 100, thereby allowing for greater flexibility of MD 100 than when using a pre-programmed chip. In some examples, processing module 106 may further include a memory circuit and processing module 106 may store information on and read information from the memory circuit. In other examples, MD 100 may include a separate memory circuit (not shown) that is in communication with processing module 106, such that processing module 106 may read and write information to and from the separate memory circuit.

Telemetry module 108 may be configured to communicate with devices such as sensors, other medical devices, or the like, that are located externally to MD 100. Such devices may be located either external or internal to the patient's body. Irrespective of the location, external devices (i.e. external to the MD 100 but not necessarily external to the patient's body) can communicate with MD 100 via telemetry module 108 to accomplish one or more desired functions. For example, MD 100 may communicate sensed electrical signals to an external medical device through telemetry module 108. The external medical device may use the communicated electrical signals in determining occurrences of arrhythmias. MD 100 may additionally receive sensed electrical signals from the external medical device through telemetry module 108, and MD 100 may use the received sensed electrical signals in determining occurrences of arrhythmias. Telemetry module 108 may be configured to use one or more methods for communicating with external devices. For example, telemetry module 108 may communicate via radiofrequency (RF) signals, inductive coupling, optical signals, acoustic signals, conducted communication signals, or any other signals suitable for communication. Communication techniques between MD 100 and external devices will be discussed in further detail with reference to FIG. 3 below.

Battery 110 may provide a power source to MD 100 for its operations. In one example, battery 110 may be a non-rechargeable lithium-based battery. In other examples, the non-rechargeable battery may be made from other suitable materials know in the art. Because, in examples where MD 100 is an implantable device, access to MD 100 may be limited, it is necessary to have sufficient capacity of the battery to deliver sufficient therapy over a period of treatment such as days, weeks, months, or years. In other examples, battery 110 may a rechargeable lithium-based battery in order to facilitate increasing the useable lifespan of MD 100.

In general, MD 100 may be similar to one of a number of existing medical devices. For example, MD 100 may be similar to various implantable medical devices. In such examples, housing 120 of MD 100 may be implanted in a transthoracic region of the patient. Housing 120 may generally include any of a number of known materials that are safe for implantation in a human body and may, when implanted, hermetically seal the various components of MD 100 from fluids and tissues of the patient's body.

In some examples, MD 100 may be an implantable cardiac pacemaker (ICP). In such an example, MD 100 may have one or more leads, for example leads 112, which are implanted in or within the patient's heart. The one or more leads 112 may include one or more electrodes 114 that are in contact with cardiac tissue and/or blood of the patient's heart. MD 100 may also be configured to sense intrinsically generated cardiac electrical signals and determine, for example, one or more cardiac arrhythmias based on analysis of the sensed signals. MD 100 may further be configured to deliver CRT, ATP therapy, bradycardia therapy, defibrillation therapy and/or other therapy types via leads 112 implanted within the heart.

In some instances, MD 100 may be a subcutaneous cardioverter-defibrillator (S-ICD). In such examples, one of leads 112 may include a subcutaneously implanted lead. In some cases, MD 100 may be configured to sense intrinsically generated cardiac electrical signals and determine one or more cardiac arrhythmias based on analysis of the sensed signals. MD 100 may further be configured to deliver one or more defibrillation pulses in response to determining an arrhythmia.

Figure 2:
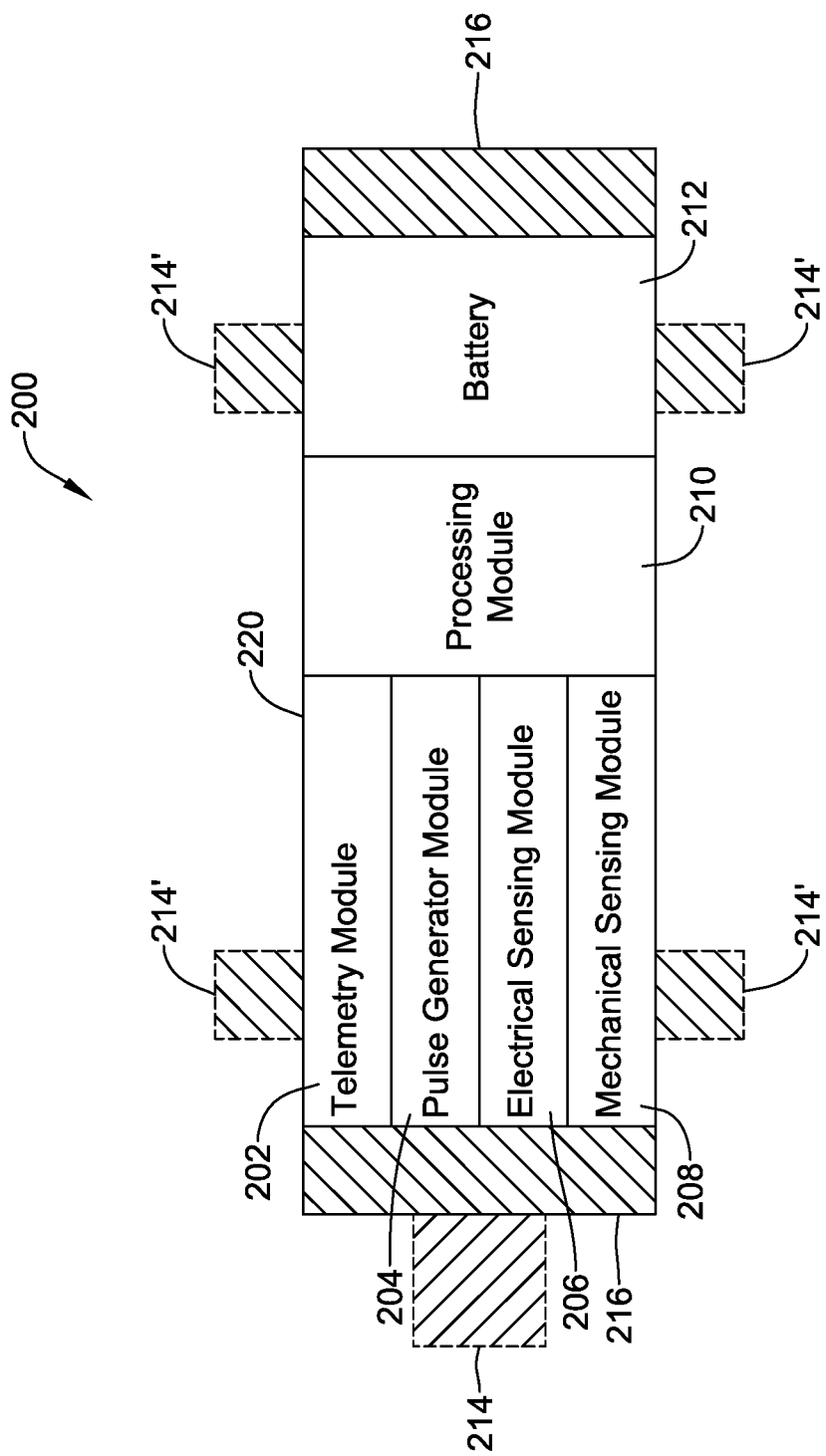
FIG. 2 illustrates an exemplary leadless cardiac pacemaker (LCP) having electrodes, according to one example of the present disclosure.

In still other examples, MD 100 may be a leadless cardiac pacemaker (LCP—described more specifically with respect to FIG. 2). In such examples, MD 100 may not include leads 112 that extend away from housing 120. Rather, MD 100 may include electrodes 114 coupled relative to the housing 120. In these examples, MD 100 may be implanted on or within the patient's heart at a desired location, and may be configured to deliver CRT, ATP therapy, bradycardia therapy, and/or other therapy types via electrodes 114.

In some instances, MD 100 may be a diagnostic-only device. In some cases, MD 100 may be configured to sense, or receive, cardiac electrical signals and/or physical parameters such as mechanical contraction, heart sounds, blood pressure, blood-oxygen levels, etc. MD 100 may further be configured to determine occurrences of arrhythmias based on the sensed or received cardiac electrical signals and/or physical parameters. In one example, MD 100 may do away with pulse generation module 104, as MD 100 may not be configured to deliver electrical stimulation in response to determining an occurrence of an arrhythmia. Rather, in order to respond to detected cardiac arrhythmias, MD 100 may be part of a system of medical devices. In such a system, MD 100 may communicate information to other devices within the system and one or more of the other devices may take action, for example delivering electrical stimulation therapy, in response to the receive information from MD 100. The term pulse generator may be used to describe any such device that is capable of delivering electrical stimulation therapy to the heart, such as an ICD, ICP, LCP, or the like. In some instances, the MD 100 may be a neural stimulation device, or any other medical device, as desired.

In some example, MD 100 may not be an implantable medical device. Rather, MD 100 may be a device external to the patient's body, and may include skin-electrodes that are placed on a patient's body. In such examples, MD 100 may be able to sense surface cardiac electrical signals (e.g. electrical signals that are generated by the heart or device implanted within a patient's body and conducted through the body to the skin). In such examples, MD 100 may still be configured to deliver various types of electrical stimulation therapy. In other examples, however, MD 100 may be a diagnostic-only device, a neurostimulator, and/or other implantable medical devices.

FIG. 2 is an illustration of an exemplary leadless cardiac pacemaker (LCP) 200. In the example shown, LCP 200 may include all of the modules and components of MD 100, except that LCP 200 may not include leads 112. As can be seen in FIG. 2, LCP 200 may be a compact device with all components housed within LCP 200 or directly on housing 220. As illustrated in FIG. 2, LCP 200 may include telemetry module 202, pulse generator module 204, processing module 210, and battery 212. Such components may have a similar function to the similarly named modules and components as discussed in conjunction with MD 100 of FIG. 1.

In some examples, LCP 200 may include electrical sensing module 206 and mechanical sensing module 208. Electrical sensing module 206 may be similar to sensing module 102 of MD 100. For example, electrical sensing module 206 may be configured to receive electrical signals generated intrinsically by the heart. Electrical sensing module 206 may be in electrical connection with electrodes 214, which may conduct the intrinsically generated electrical signals to electrical sensing module 206. Mechanical sensing module 208 may be configured to receive one or more signals representative of one or more physiological parameters of the heart. For example, mechanical sensing module 208 may include, or be in electrical communication with one or more sensors, such as accelerometers, blood pressure sensors, heart sound sensors, blood-oxygen sensors, and other sensors which measure physiological parameters of the patient. Although described with respect to FIG. 2 as separate sensing modules, in some examples, electrical sensing module 206 and mechanical sensing module 208 may be combined into a single module.

In at least one example, each of modules 202, 204, 206, 208, and 210 illustrated in FIG. 2 may be implemented on a single integrated circuit chip. In other examples, the illustrated components may be implemented in multiple integrated circuit chips that are in electrical communication with one another. All of modules 202, 204, 206, 208, and 210 and battery 212 may be encompassed within housing 220. Housing 220 may generally include any material that is known as safe for implantation within a human body and may hermetically seal modules 202, 204, 206, 208, and 210 and battery 212 from fluids and tissues when LCP 200 is implanted within a patient.

As depicted in FIG. 2, LCP 200 may include electrodes 214, which can be secured relative to housing 220 but exposed to the tissue and/or blood surrounding the LCP 200. As such, electrodes 214 may be generally disposed on either end of LCP 200 and may be in electrical communication with one or more of modules 202, 204, 206, 208, and 210. In some examples, electrodes 214 may be connected to housing 220 only through short connecting wires such that electrodes 214 are not directly secured relative to housing 220. In some examples, LCP 200 may additionally include one or more electrodes 214'. Electrodes 214' may be positioned on the sides of LCP 200 and increase the number of electrodes by which LCP 200 may sense cardiac electrical activity and/or deliver electrical stimulation. Electrodes 214 and/or 214' can be made up of one or more biocompatible conductive materials such as various metals or alloys that are known to be safe for implantation within a human body. In some instances, electrodes 214 and/or 214' connected to LCP 200 may have an insulative portion that electrically isolates the electrodes 214 from, adjacent electrodes, the housing 220, and/or other materials.

To implant LCP 200 inside patient's body, an operator (e.g., a physician, clinician, etc.), may need to affix LCP 200 to the cardiac tissue of the patient's heart. To facilitate fixation, LCP 200 may include one or more anchors 216. Anchor 216 may be any one of a number of fixation or anchoring mechanisms. For example, anchor 216 may include one or more pins, staples, threads, screws, helix, tines, and/or the like. In some examples, although not shown, anchor 216 may include threads on its external surface that may run along at least a partial length of anchor 216. The threads may provide friction between the cardiac tissue and the anchor to help fix anchor 216 within the cardiac tissue. In other examples, anchor 216 may include other structures such as barbs, spikes, or the like to facilitate engagement with the surrounding cardiac tissue.

The design and dimensions of MD 100 and LCP 200, as shown in FIGS. 1 and 2, respectively, can be selected based on various factors. For example, if the medical device is for implant on the endocardial tissue, such as is sometimes the case of an LCP, the medical device can be introduced through a femoral vein into the heart. In such instances, the dimensions of the medical device may be such as to be navigated smoothly through the tortuous path of the vein without causing any damage to surrounding tissue of the vein. According to one example, the average diameter of the femoral vein may be between about 4 millimeters (mm) to about 8 mm. For navigation to the heart through the femoral vein, the medical device can have a diameter of less than 8 mm In some examples, the medical device can have a cylindrical shape having a circular cross-section. However, it should be noted that the medical device can be made of any other suitable shape such as rectangular, oval, etc. A flat, rectangular-shaped medical device with a low profile may be desired when the medical device is designed to be implanted subcutaneously.

While IMD 100 and LCP 200 are described as suitable example medical devices, it is contemplated that the present disclosure is applicable more broadly to communication between any two (or more) medical devices.

Figure 3:
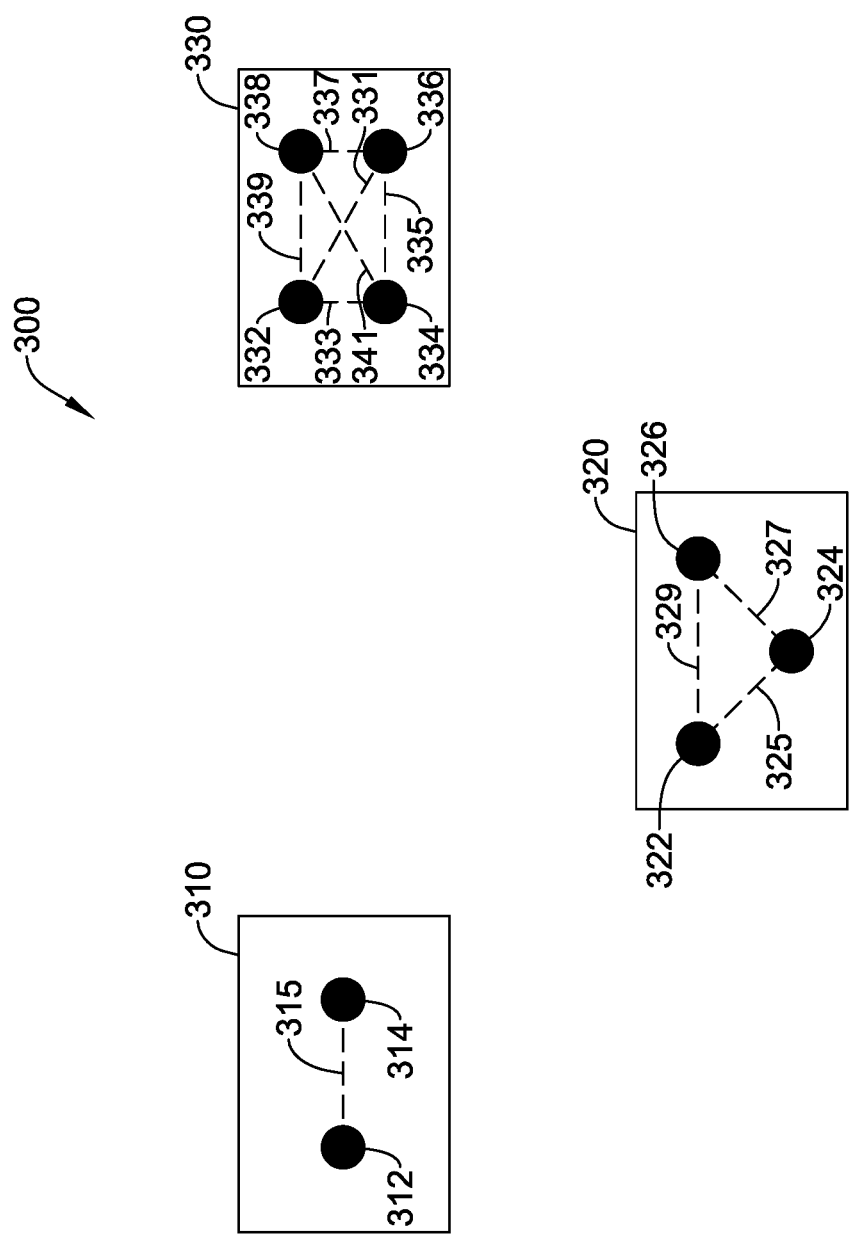
FIG. 3 shows an illustrative system that includes several medical devices in accordance with the present disclosure.

FIG. 3 is a schematic illustration of a medical device system 300. As illustrated, medical device system 300 includes a first MD 310, a second MD 320 and a third MD 330. Each of MD 310, MD 320 and MD 330 can represent any of a variety of different medical devices that are configured to deliver electrical stimulation, pacing pulses, defibrillation pulses, or the like in order to implement one or more therapies, such as ATP therapy, CRT, or other electrical stimulation therapies, or are diagnostic only or other medical devices, as desired. Each of MD 310, MD 320 and MD 330 can include leads or be leadless. It will be appreciated that while three medical devices are shown in FIG. 3, system 300 may include just one or two medical devices, or may include four or more medical devices, depending on the particular application.

In some embodiments, each of MD 310, MD 320 and MD 330, if present, may be implanted and/or positioned proximate the patient. In some embodiments, MD 310 may be implanted, MD 320 may be external to the patient and MD 330 may be optional. MD 320 may include a skin patch including two or more electrodes. In some cases, one or more of MD 310, MD 320 and MD 330 may be a medical device programmer or communicator that is configured to communicate with and/or program one or more implanted medical device. For example, MD 320 may be a medical device programmer or communicator that is configured to communicate with and/or program one or more implanted medical device—such as MD 310 and MD 330. In some embodiments, MD 310 may be implanted within the patient and MD 320 and/or MD 330 may also be implanted within the patient but be spaced apart from MD 310 and from each other.

As illustrated, MD 310 includes a first electrode 312 and a second electrode 314. MD 320 includes a first electrode 322, a second electrode 324 and a third electrode 326. MD 330 includes a first electrode 332, a second electrode 334, a third electrode 336 and a fourth electrode 338. In this example, MD 310 has a single electrode pair 315 that can be used to sense, pace and/or communicate with another medical device. MD 320 has a first electrode pair 325 between first electrode 322 and second electrode 324, a second electrode pair 327 between second electrode 324 and third electrode 326, and a third electrode pair 329 between first electrode 322 and third electrode 326 that can each be used, either individually or in combination, to sense, pace and/or communicate with another medical device. MD 330 has a first electrode pair 333 between first electrode 332 and second electrode 334, a second electrode pair 335 between second electrode 334 and third electrode 336, a third electrode pair 337 between third electrode 336 and fourth electrode 338, a fourth electrode pair 339 between first electrode 332 and fourth electrode 338, a fifth electrode pair 331 between first electrode 332 and third electrode 336 and a sixth electrode pair 341 between second electrode 334 and fourth electrode 338 that can each be used, either individually or in combination, to sense, pace and/or communicate with another medical device.

Figure 4:
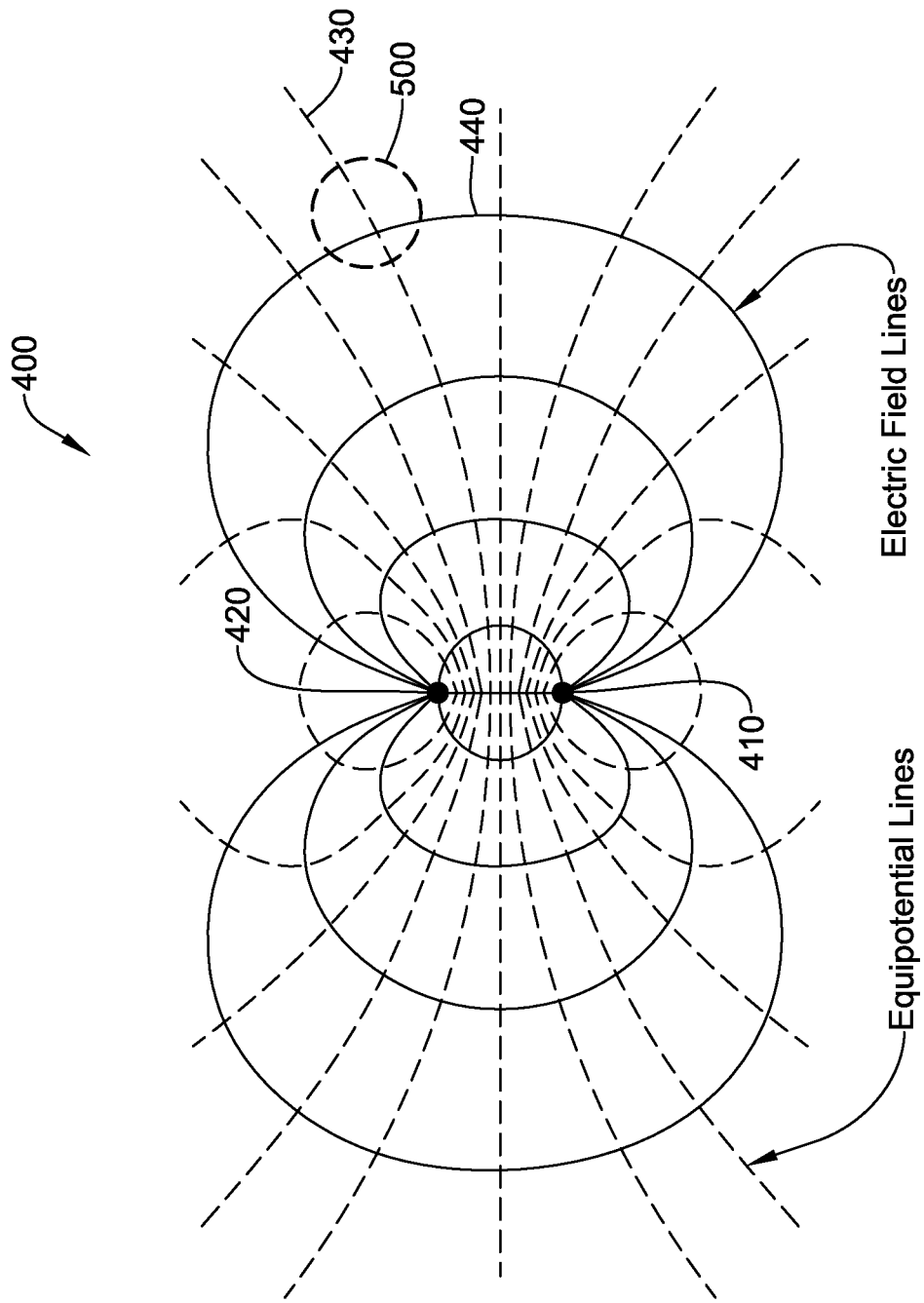
FIG. 4 is a diagram of an illustrative electromagnetic field that may be generated by an electrode pair.
Figure 5:
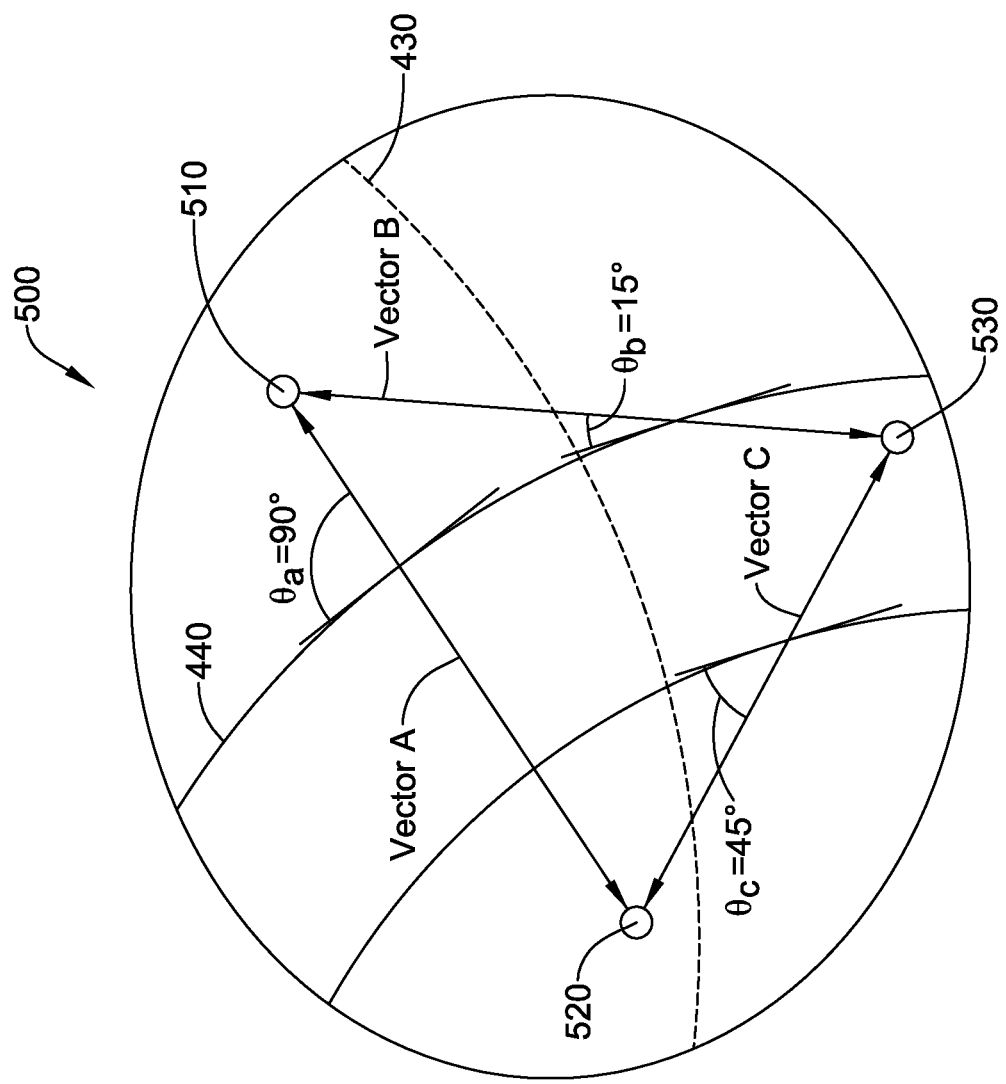
FIG. 5 is a diagram of a portion of the electromagnetic field of FIG. 4, illustrating different geometric arrangements of electrodes relative to the electromagnetic field.

It will be appreciated that the relative signal strength received at a particular electrode pair can be a function of, at least in part, the relative orientation of the electrode pair relative to the electromagnetic field that is being generated by a transmitting electrode pair. FIG. 4 is a stylized or idealized electromagnetic field 400 generated by an electrode pair, which includes a cathode electrode 410 and an anode electrode 420. This is a stylized electromagnetic field 400 as it would appear in a homogenous conducting medium. As the patient's tissue near and around medical devices is not homogenous, the actual electromagnetic field would vary from that shown. The electromagnetic field 400 can be considered as including equipotential lines 430 and electric field lines 440. FIG. 5 provides an enlarged portion 500 illustrating the effects of electrode orientation relative to the equipotential lines 430 and the electric field lines 440.

In the illustration of FIG. 5, it is assumed that a medical device includes a first electrode 510, a second electrode 520 and a third electrode 530. A first electrode pair vector A may be considered as existing between first electrode 510 and second electrode 520. A second electrode pair vector B may be considered as existing between first electrode 510 and third electrode 530. A third electrode pair vector C may be considered as existing between second electrode 520 and third electrode 530. It will be appreciated that the relative signal strength between one of electrode pair vectors A, B and C will be influenced by the angle between the receiving antenna (one of the electrode pair vectors A, B and C) and the local electric field produced by the transmitting antenna (cathode 410 and anode 420 as shown in FIG. 4). As can be seen, the received signal will be the signal strength times the cosine of the angle θ between the corresponding electrode pair vector A, B or C and the electric field lines 440. The electrode pair vectors each represent a pair of electrodes of the medical device. A particular one the electrode pairs A, B, or C selected for communication, in combination with an electrode pair of the transmitting antenna (e.g. cathode 410 and anode 420 as shown in FIG. 4) can be considered a "communication vector".

As illustrated, electrode pair vector A forms an angle $\theta_A$ that is 90 degrees. As the cosine of 90 degrees is zero, electrode pair vector A (between first electrode 510 and second electrode 520) would not receive a signal. Electrode pair vector B forms an angle $\theta_B$ that is 15 degrees. The cosine of 15 degrees is 0.97, and thus electrode pair vector B would receive a signal that is 97% of the strength of the signal at that location. Electrode pair vector C forms an angle θc that is 45 degrees. The cosine of 45 degrees is 0.71, and thus electrode pair vector C would receive a signal that is 71% of the strength of the signal at that location. It will be appreciated, therefore, that by having several electrode pairs, or electrode pair vectors, to choose from may facilitate the devices MD 310, MD 320 and MD 330 of system 300 (FIG. 3) in selecting an electrode pair or electrode pair vector that helps increase the relative signal strength and/or signal-to-noise ratio for communication therebetween. The angles shown in FIG. 5 are illustrative only, as in practice the medical device that includes electrodes 510, 520 and 530 may have any particular orientation with respect to electromagnetic field 400 (FIG. 4), and the orientation may change over time as the patient breathes, the heart pumps, or the patient otherwise moves. It is contemplated that a medical device may have two, three, four or more electrodes that can be utilized in pairs to help improve communication between medical devices.

Figure 6:
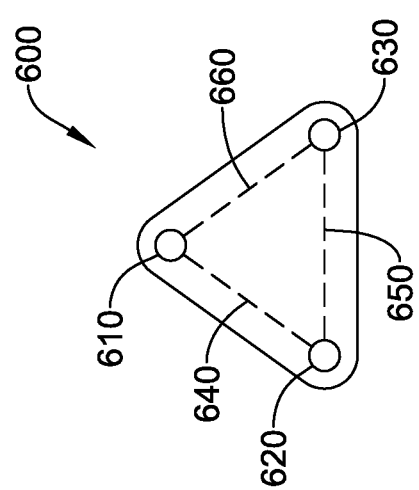
FIG. 6 is a schematic diagram of a medical device having an illustrative antenna with three electrodes in accordance with various examples of the present disclosure.

FIG. 6 illustrates a medical device (MD) 600 that includes a first electrode 610, a second electrode 620 and a third electrode 630. A total of three electrode pair vectors 640, 650 and 660 may be formed using the three electrodes of MD 600. MD 600 may represent an implanted medical device or an external medical device. MD 600 may, in some cases, represent an external patch that is secured to the skin of a patient, and may communicate with an implanted medical device such as a leadless cardiac pacemaker (LCP). As illustrated, electrodes 610, 620 and 630 are equally spaced forming an equilateral triangle. In some embodiments, electrodes 610, 620 and 630 may instead be unequally spaced, thereby forming a non-equilateral triangle.

Figure 7:
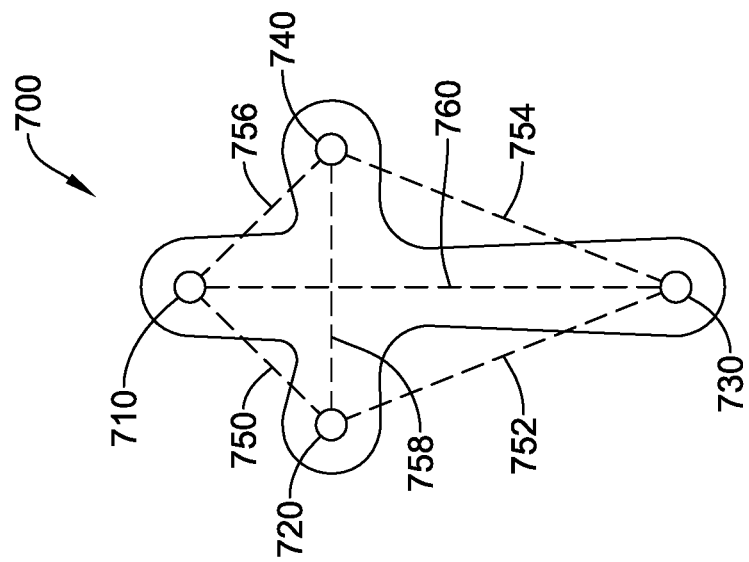
FIG. 7 is a schematic diagram of a medical device having an illustrative antenna with four electrodes in accordance with various examples of the present disclosure.

FIG. 7 illustrates a medical device (MD) 700 that includes a first electrode 710, a second electrode 720, a third electrode 730 and a fourth electrode 740. In FIG. 7, a total of 6 electrode pair vectors 750, 752, 754, 756, 758 and 760 may be formed using the electrodes of MD 700. MD 700 may represent an implanted medical device or an external medical device. MD 700 may, for example, represent an external patch that is secured to the skin of a patient. As illustrated, electrodes 710, 720, 730 and 740 are spaced about MD 700 in a kite pattern. In some embodiments, electrodes 710, 720, 730 and 740 may instead be spaced about MD 700 in a variety of different patterns. It will be appreciated that the relative angles between pairs of electrodes 710, 720, 730 and 740 may be varied by altering the relative dimensions, i.e., length and/or width of the spacings between the electrodes of MD 700.

Figure 8:
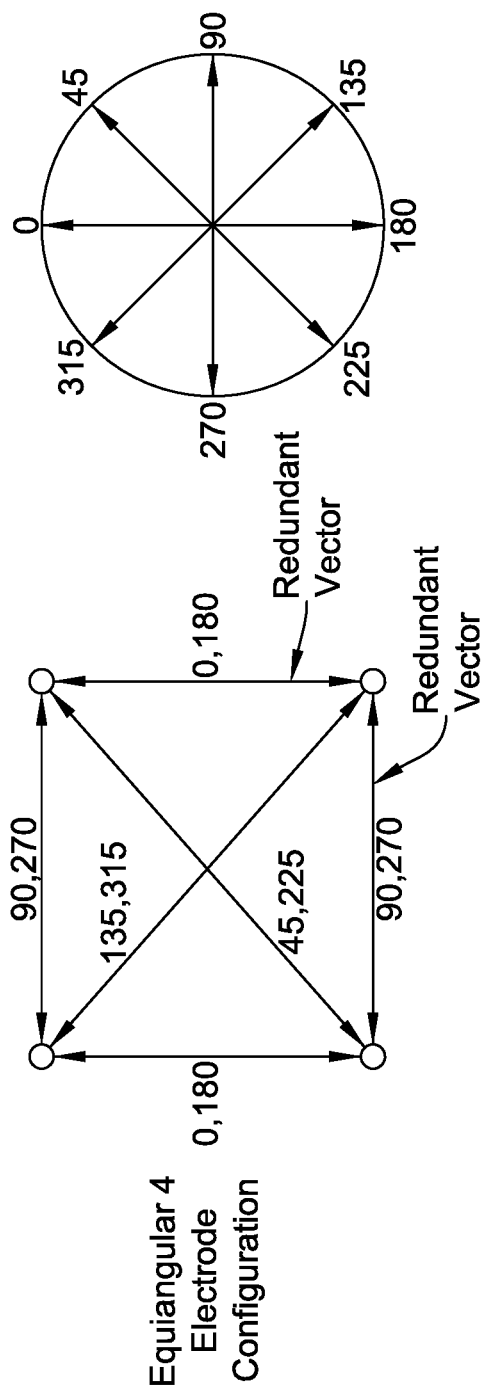
FIG. 8 is a schematic diagram of an illustrative arrangement of four electrodes in accordance with various examples of the present disclosure.
Figure 9:
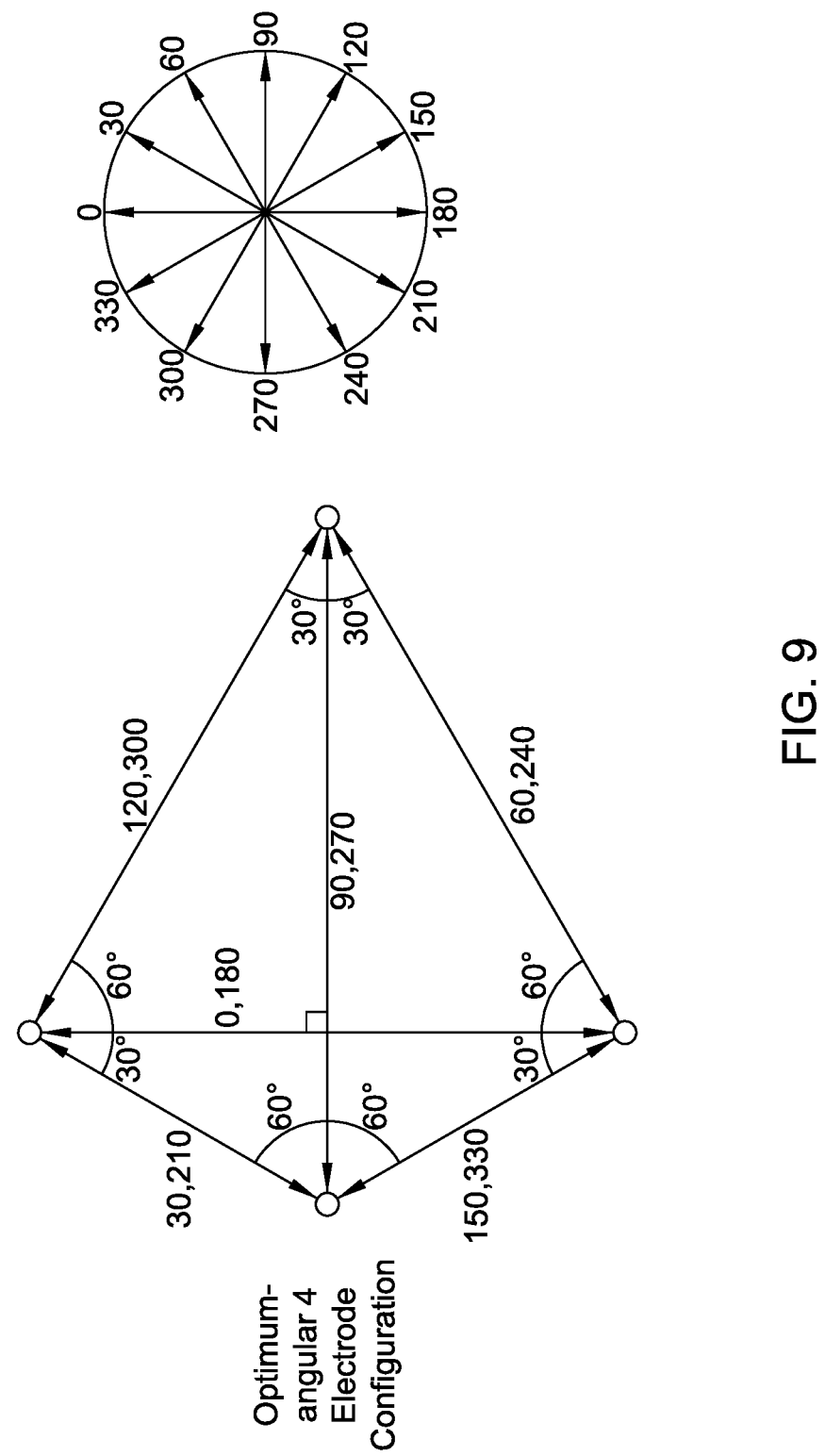
FIG. 9 is a schematic diagram of another illustrative arrangement of four electrodes in accordance with various examples of the present disclosure.

FIGS. 8 and 9 provide additional examples of possible electrode pair vector angles in medical devices having 4 electrodes arranged in a rectilinear configuration (FIG. 8) or in a kite like configuration (FIG. 9). It will be appreciated that these are illustrative only, as the angles in FIG. 8 may be altered by changing the relative length and width of a square or rectangle extending through the four electrodes. Similarly, the angles in FIG. 9 may be altered by changing the relative length and width of a kite-shape extending through the four electrodes.

It can be seen that having two electrodes can provide a situation in which there can be no or substantially no signal strength at the location of a receiving antennae, depending on orientation of the receiving antennae relative to the emitted electric field. Having three electrodes provides three possible electrode pair vectors that can be selected, whereby selecting the electrode pair vector with the greatest signal strength, may help improve the signal strength received by the receiving antennae. Having four electrodes provides six possible electrode pair vectors that can be selected. In some cases, and to provide even more vectors, two or more of the electrodes may be effectively shorted together so that the shorted electrodes collectively act as an electrode. For example, and specifically with respect to FIG. 7, electrodes 730 and 740 may be effectively shorted together and may act as a single electrode (e.g. anode), and electrode 710 or electrode 720 may act as the other electrode (e.g. the cathode). This is just one example.

In some instances, the medical devices described herein, including MD 100, LCP 200, MD 310, MD 320, MD 330, MD 600 or MD 700 may be programmed or otherwise configured to test various communication vectors and to select the appropriate communication vector for communication. In some embodiments, the strongest communication vector may be selected. In some embodiments, the weakest communication vector may be excluded from use. In some embodiments, depending on the purpose of the communication, several communication vectors may be used in combination.

In some instances, one vector may be used during a first part of a single communication and a second vector may be used during a second part of the communication. This may occur when, for example, a device programmer or an S-ICD is communicating with a LCP. The LCP may be moving during each beat of the heart, and the angles between the various electrodes may change over time. In some cases, it may be advantageous to use a first vector to start communication, and then as the LCP moves, switch to a second vector to complete the communication.

Alternatively, or in addition, communication may be simultaneously performed using two or more vectors. This may provide one or more redundant communication paths, so that if one communication path becomes less effective or drops out, then the redundant communication path(s) can be used. For example, and specifically with respect to FIG. 7, communication may be simultaneously performed using a first vector 754 extending between electrodes 730 and 740 and a second vector 758 extending between electrodes 720 and 740. Then, if communication using the first vector 754 becomes less effective or drops out, the system can still communicate using the second vector 758. In some cases, communication may be performed simultaneously using both vectors, and the system may select the communication path with the highest signal strength, the communication path that provided successful transmission, and/or may use any other criteria for selecting from the two or more communication paths. In some cases, a communication may be performed using multiple vectors, and the results may be compared. If there is no difference in the results, then either result may be used. If there is a difference, other criteria may be used to help identify the correct result. For example, a parity bit and/or checksum may be used to identify which transmissions were successful. If no transmissions were successful, a signal may be sent notifying the sender to repeat the transmission using a different vector or set of vectors.

Figure 10:
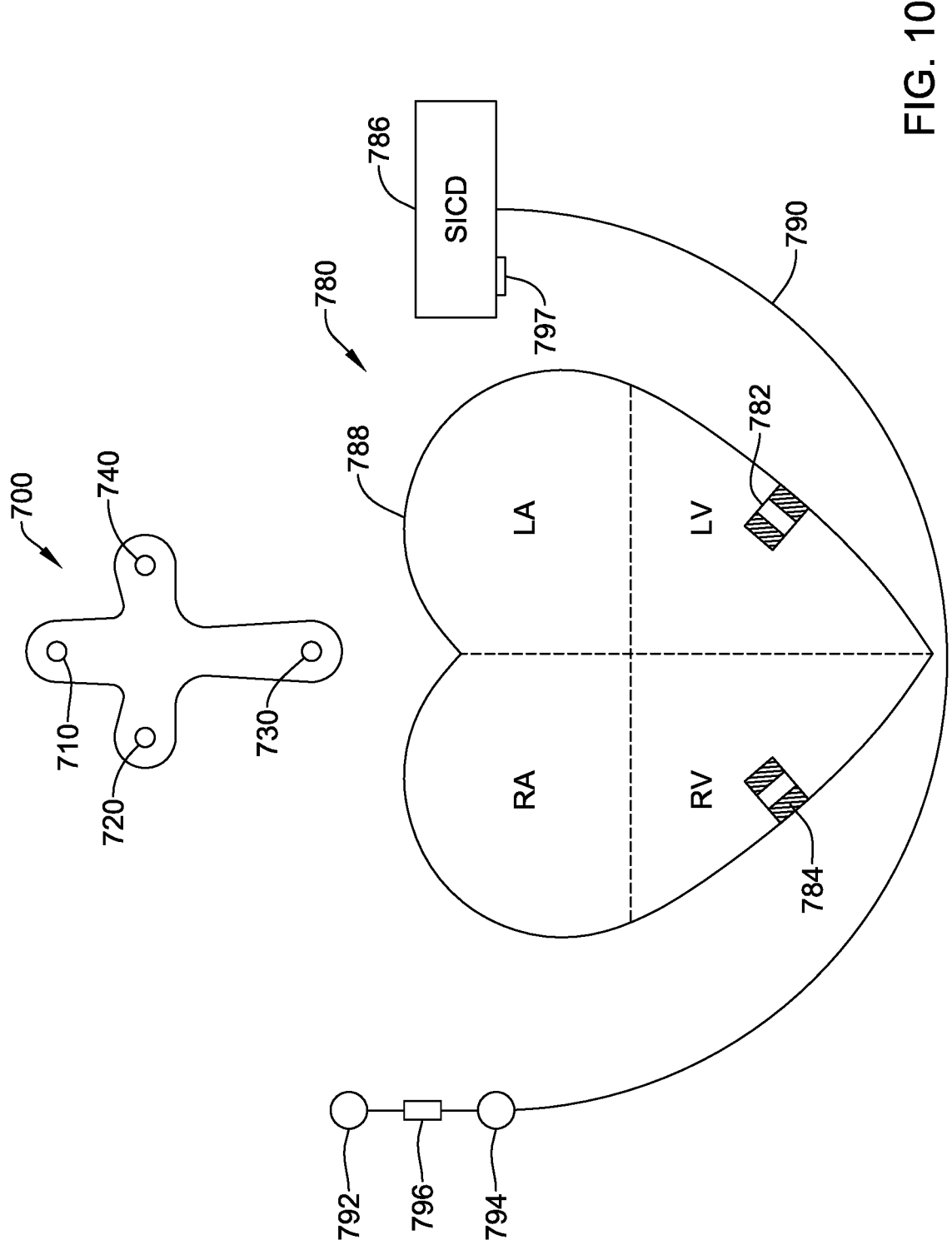
FIG. 10 shows an illustrative system in accordance with an example of the present disclosure.

FIG. 10 provides an illustrative medical system in which an LCP 782 is shown fixed to the interior of the left ventricle of a heart 788 and an LCP 784 is shown fixed to the interior of the right ventricle of heart 788. In some embodiments, there may be additional LCPs implanted in heart 788. In other cases, there may only be one LCP, such as LCP 784.

In some embodiments, one or more LCPs may be fixed to the exterior of the heart 788. In FIG. 10, an example SICD 786 is shown. The example SICD 786 includes a lead 790 bearing one or more electrodes 792, 794 and 796. In some embodiments, the lead 790 may include more than three electrodes. In some cases, once lead 790 has been implanted, electrodes 792, 794 and 796 may be considered as being aligned vertically proximate the patient's sternum. Optionally, an additional electrode may be disposed on a horizontal (once implanted) portion of lead 790. It will be appreciated that as illustrated, SICD 786 may be considered as having a total of four electrodes, as the housing of SICD 786 may also function as an electrode. In some instances, lead 790 may be positioned subcutaneously adjacent heart 788. In some cases, the illustrative medical system may include an external patch such as MD 700 previously discussed with respect to FIG. 7 for connecting to, for example, an external medical device.

In some cases, there may be a desire for communication between two or more of LCP 782, LCP 784, SICD 786 and/or an MD 700. It will be appreciated, for example, that for communication between the LCP 782 and MD 700, there may be a total of four (or more) electrodes on MD 700 and two to four (or more) electrodes on LCP 782, and thus many different communication vectors may be tested and selected as discussed previously. In some cases, particularly in conducting communication between SICD 786 and any of the other devices shown, it will be appreciated that electrodes 792, 794 and 796 are arranged in a largely linear fashion near a distal end of lead 790. Accordingly, in some cases, selecting between these three electrodes for use in a communication vector with an LCP 872 or 784 may not substantially change the geometry of the vector and thus may not substantially improve the communication vector. In some embodiments, communication with SICD 786 may benefit from also considering one or more can electrodes, such as can electrode 797 of the SICD 786. When so provided, the SICD may have four different electrodes 792, 794, 796 and 797, and each LCP 782 and 784 may have two to four (or more) electrodes. This may provide many vectors to choose from with a variety of different vector geometries. Alternatively, or in addition, the SICD electrodes 792, 794 and 796 may be arranged in a non-linear manner, such as in a cross-pattern.

One or all of the electrodes 792, 794, 796, 797 and the SCID 786 housing may be used only for communication; alternatively one or all of the electrodes 792, 794, 796, 797 and the SCID 786 housing may also be used for other purposes such as sensing a physiological parameter (e.g. intrinsic cardiac activity, thoracic impedance) and/or delivering one or more electrical therapies (e.g. cardioversion/defibrillation shocks, cardiac paces, neural stimulation energy).

In some cases, it will be appreciated that which specific vector or vectors are most useful for communicating between any particular pair of devices may change over time. For example, LCP 782 and/or LCP 784, if present, may move and change orientation somewhat with each heartbeat. As the patient breathes, and their chest rises and falls, the SICD 786 and an external device such as MD 700 may also move. Accordingly, in some embodiments, it may be advantageous to use a first vector for part of a communication, and then as one or more devices move relative to one another, such as with the heartbeat and/or patient respiration, switch to a second vector to continue the communication. In some cases, signal strength, error rate and/or communication parameter may be monitored over time, and the vector may be automatically switched if desired. While a first and second vector are used here an example, it is contemplated that the system may switch between more than two different vectors if desired. It is contemplated that the vectors may be switched in real or near real time, and/or may be updated from time to time, e.g. every minute, hour, day, month, each doctor visit, and/or any other suitable time.

Figure 11:
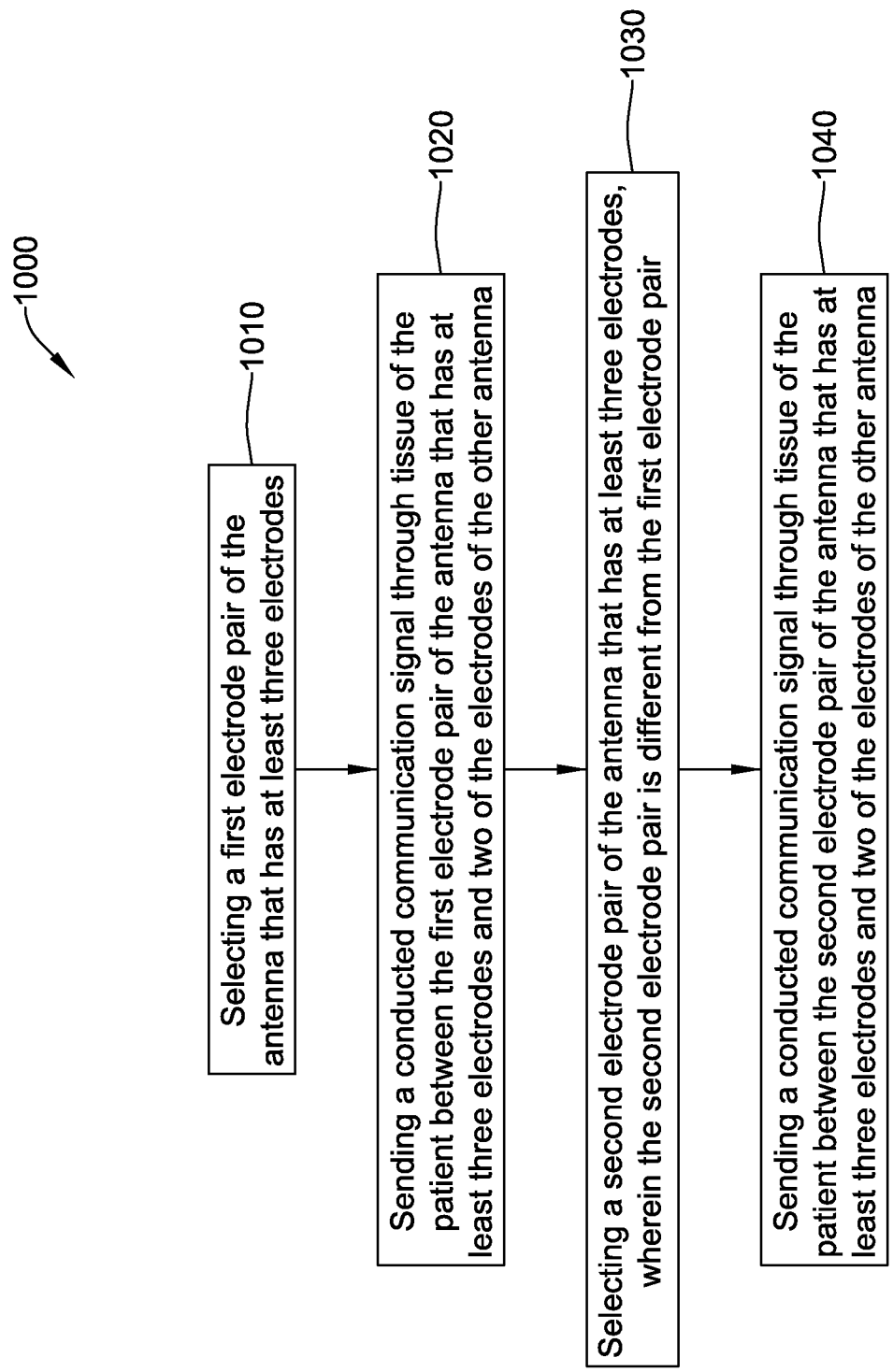
FIG. 11 is a flow diagram of an illustrative method for communicating between medical devices.

FIG. 11 is a flow diagram showing an illustrative method 1000 that may be carried out via any of the medical devices described herein, including MD 100, LCP 200, MD 310, MD 320, MD 330, MD 600 or MD 700. At block 1010, a first electrode pair of an antenna having at least three electrodes is selected. A communication signal, such as a conducted communication signal, may be sent through tissue of the patient between the first electrode pair of the antenna having at least three electrodes and two electrodes of another antenna, as generally seen at block 1020. At block 1030, a second electrode pair of the antenna having at least three electrodes is selected. The second electrode pair selected being different from the first selected electrode pair. A communication signal is again sent through tissue of the patient between the first electrode pair of the antenna having at least three electrodes and two electrodes of another antenna, as generally seen at block 1040.

Figure 12:
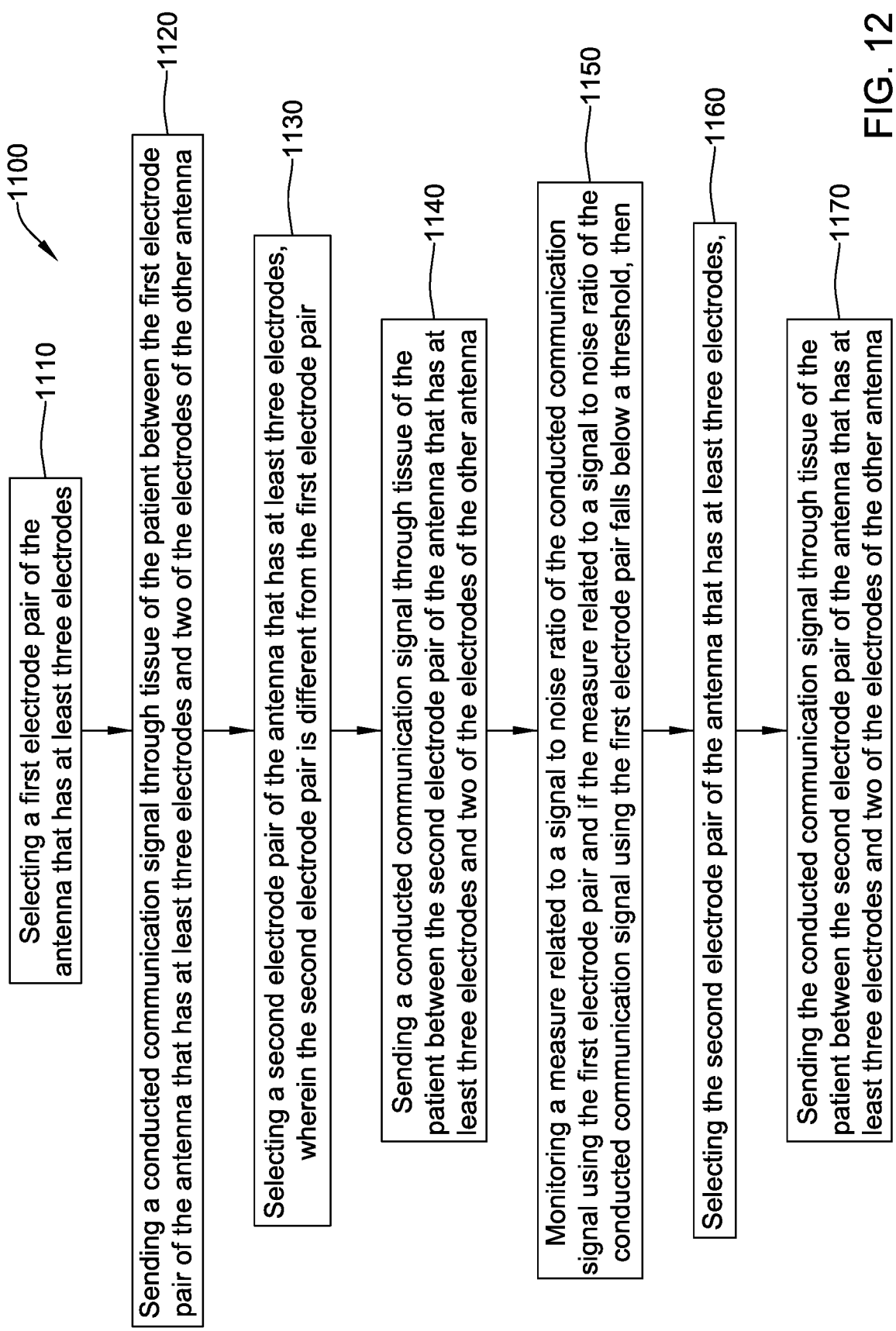
FIG. 12 is a flow diagram showing another illustrative method for communicating between medical devices.

FIG. 12 is a flow diagram showing an illustrative method 1100 that may be carried out via any of the medical devices described herein, including MD 100, LCP 200, MD 310, MD 320, MD 330, MD 600 or MD 700. At block 1110, a first electrode pair of an antenna having at least three electrodes is selected. A communication signal is sent through tissue of the patient between the first electrode pair of the antenna having at least three electrodes and two electrodes of another antenna, as generally seen at block 1120. At block 1130, a second electrode pair of the antenna that has at least three electrodes is selected. The second electrode pair is different from the first selected electrode pair. A communication signal may be sent through tissue of the patient between the first electrode pair of the antenna having at least three electrodes and two electrodes of another antenna, as generally seen at block 1140.

During operation, and as seen at block 1150, a measure related to a signal-to-noise ratio of the conducted communication signal using the first electrode pair may be monitored. If the measure related to the signal-to-noise ratio falls below a threshold or changes by more than a threshold, the second electrode pair of the antenna having at least three electrodes is selected, as generally shown at block 1160. At block 1170, a communication signal may then be sent through tissue of the patient between the second electrode pair of the antenna having at least three electrodes and the two electrodes of the other antenna.

Figure 13:
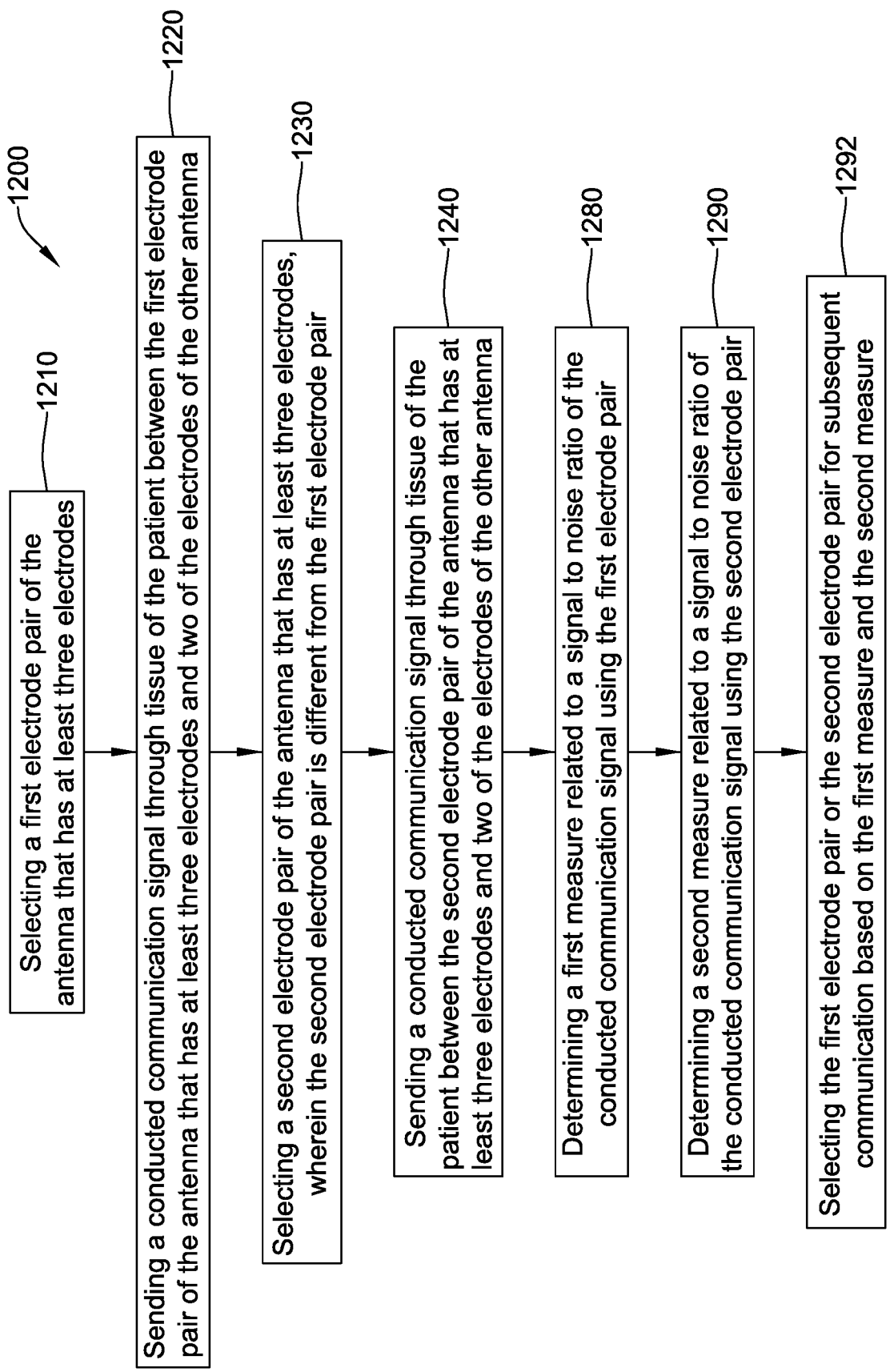
FIG. 13 is a flow diagram showing yet another illustrative method for communicating between medical devices.

FIG. 13 is a flow diagram showing an illustrative method 1200 that may be carried out via any of the medical devices described herein, including MD 100, LCP 200, MD 310, MD 320, MD 330, MD 600 or MD 700. At block 1210, a first electrode pair of an antenna having at least three electrodes is selected. A communication signal is sent through tissue of the patient between the first electrode pair of the antenna having at least three electrodes and two electrodes of another antenna, as generally seen at block 1220. At block 1230, a second electrode pair of the antenna that has at least three electrodes is selected. The second electrode pair is different from the first selected electrode pair. A communication signal is sent through tissue of the patient between the first electrode pair of the antenna having at least three electrodes and two electrodes of another antenna, as generally seen at block 1240.

During operation, and as block 1280, a first measure related to a signal-to-noise ratio of the communication signal using the first electrode pair is determined. A second measure related to a signal-to-noise ratio of the communication signal using the second electrode pair is determined, as generally indicated at block 1290. At block 1292, the first electrode pair or the second electrode pair is selected for subsequent communication based on the first measure and the second measure.

Figure 14:
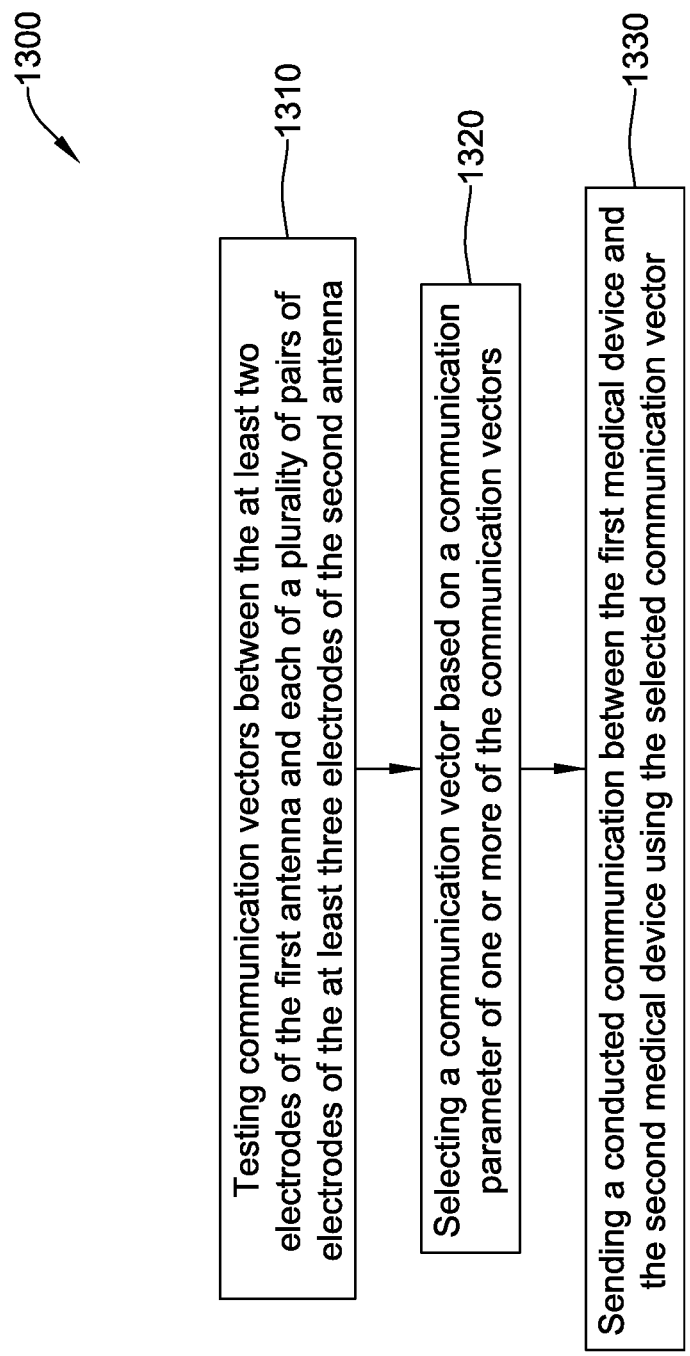
FIG. 14 is a flow diagram showing another illustrative method for communicating between medical devices.

FIG. 14 a flow diagram showing an illustrative method 1300 that may be carried out via any of the medical devices described herein, including MD 100, LCP 200, MD 310, MD 320, MD 330, MD 600 or MD 700. At block 1310, communication vectors are tested between at least two electrodes of a first antenna and each of a plurality of pairs of electrodes of a second antenna that has at least three electrodes. In an embodiment, a communication vector is tested periodically, for example once per second, minute, day or month. In another embodiment, a communication vector is tested only when a communication parameter fails to meet a predetermined criteria. In some embodiments, a communication vector is tested during an office visit. In other embodiments, a communication vector is tested during an interaction between a medical device and an external system that is configured to provide device or patient data to a clinician at a remote location. A communication vector is selected based on a communication parameter of one or more of the communication vectors, as generally indicated at block 1320. The communication parameter could, for example, be an absolute signal strength, a relative signal strength and/or a signal-to-noise ratio, or any other parameter affecting or potentially affecting communication. At block 1330, a conducted communication is sent between a first medical device and a second medical device using the selected communication vector.

As detailed above, the medical devices referenced herein may by any suitable medical device. In some non-limiting example, the methods 1000, 1100, 1200, 1300 may be used in communication between an LCP and a medical device programmer or communicator, an LCP and an Sub-coetaneous Implantable Cardioverter Defibrillator (SICD), an LCP and a co-implanted diagnostic device, an LCP and a neurostimulator device, an LCP and another LCP, and/or between any other suitable medical devices, as desired.

In some embodiments, any of these methods described herein could embody receiving a communication instead or, or in addition to, sending a communication signal. In some embodiments, a selection or determination of a communication vector used for sending a communication signal may be the same as a communication vector used for receiving a communication signal. In some embodiments, a selection or determination of a communication vector used for sending a communication signal may be different than a communication vector used for receiving a communication signal.

Those skilled in the art will recognize that the present disclosure may be manifested in a variety of forms other than the specific embodiments described and contemplated herein. As one example, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed is:

1. A communication system, comprising:
   a first medical device having at least two electrodes that are associated with the first medical device;
   a second medical device including a plurality of electrodes defining at least a first communication vector using a first pair of electrodes of the plurality of electrodes and a second communication vector using a second pair of electrodes of the plurality of electrodes;
   the second medical device configured to listen for messages from the first medical device via the first communication vector and to listen for the same messages from the first medical device via the second communication vector;
   the second medical device monitoring a first measure related to a signal-to-noise ratio of the conducted communication via the first communication vector and monitoring a second measure related to the signal-to-noise ratio of the conducted communication via the second communications vector; and
   the second medical device comparing results of the conducted communication via the first communication vector to results of the conducted communication via the second communications vector, and when the results do not match, identifying the correct result based on one or more criteria.

2. The system of claim 1, wherein the second medical device is configured to transmit messages to the first medical device using the first communication vector, the second communication vector, or both the first communication vector and the second communication vector.

3. The system of claim 1, wherein the first medical device comprises an implantable medical device.

4. The system of claim 1, wherein the first medical device comprises a leadless cardiac pacemaker (LCP).

5. The system of claim 1, wherein the plurality of electrodes comprise four electrodes secured to a skin patch, the four electrodes arranged on the skin patch in a kite configuration having a first pair of equal-length adjacent sides and a second pair of equal-length adjacent sides that are of a different length than the first pair of equal-length adjacent sides, the skin patch being configured to be secured to a patient's skin such that each of the four electrodes is in electrical contact with the patient's skin and assume a fixed position relative to the patient for communicating with the first medical device.

6. The system of claim 5, wherein having the four electrodes arranged on the skin patch in a kite configuration provides a consistent and predictable set of communication vectors including the first communication vector and the second communication vector.

7. A method of communicating between a first medical device and a second medical device, the first medical device implanted within a patient and having at least two electrodes and the second medical device being associated with a skin patch that includes a plurality of electrodes, wherein the skin patch is secured to a patient's skin such that each of the plurality of electrodes of the skin patch are in electrical contact with the patient's skin, the plurality of electrodes of the skin patch defining at least a first communication vector using a first pair of electrodes of the plurality of electrodes of the skin patch and a second communication vector using a second pair of electrodes of the plurality of electrodes of the skin patch, the method comprising:
   receiving at the second medical device a message sent by conducted communication from the first medical device using the first communication vector;

receiving at the second medical device the same message sent by conducted communication from the first medical device using the second communication vector;

monitoring a first measure related to a signal-to-noise ratio of the conducted communication via the first communication vector and monitoring a second measure related to the signal-to-noise ratio of the conducted communication via the second communications vector; and comparing results of the conducted communication via the first communication vector to results of the conducted communication via the second communications vector, and when the results do not match, selecting the message received via the communication vector with the highest indicated signal-to-noise ratio.

8. The method of claim 7, wherein the first pair of electrodes do not share an electrode with the second pair of electrodes.

9. The method of claim 7, wherein the first pair of electrodes share an electrode with the second pair of electrodes.

10. The method of claim 7, wherein when there is not the match, switching out one of the communication vectors with a third communication vector that uses a third pair of electrodes of the plurality of electrodes of the skin patch.

11. The method of claim 7, wherein the skin patch comprising a plurality of electrodes includes a patch periphery and four electrodes disposed within the patch periphery, wherein the four electrodes are aligned in a predetermined pattern forming a kite-shaped electrode arrangement.

12. The method of claim 11, wherein the four electrodes are aligned in a kite configuration having a first pair of equal-length adjacent sides and a second pair of equal-length adjacent sides that are of a different length than the first pair of equal-length adjacent sides in order to define a set of predictable communication vectors including the first communication vector and the second communication vector.

13. The method of claim 12, wherein the set of predictable communication vectors include a pair of communication vectors that are orthogonal to each other.

14. The method of claim 7, wherein the second medical device is an external medical device operatively coupled to the skin patch.

15. A method of communicating between an implantable medical device having at least two electrodes and an external medical device associated with a skin patch bearing a plurality of electrodes that define at least a first communication vector utilizing a first pair of the plurality of electrodes of the skin patch and a second communication vector utilizing a second pair of the plurality of electrodes of the skin patch, the method comprising:

securing the skin patch to the patient's skin such that the plurality of electrodes are in electrical contact with the patient's skin;

receiving a message via conducted communication at the external medical device using the first communication vector sent from the implantable medical device;

simultaneously receiving the same message via conducted communication at the external medical device using the second communication vector sent from the implantable medical device;

monitoring a signal-to-noise ratio of the conducted communication via the first communication vector and monitoring the signal-to-noise ratio of the conducted communication via the second communications vector; and comparing results of the conducted communication via the first communication vector to results of the conducted communication via the second communications vector, and when the results do not match, selecting the message received via the communication vector with the highest indicated signal-to-noise ratio.

16. The method of claim 15, further comprising continuing to communicate via the first communication vector or the second communication vector if the other of the first communication vector or the second communication vector becomes unreliable.

* * * * *